(12) United States Patent
Tzeng et al.

(10) Patent No.: US 8,338,160 B2
(45) Date of Patent: *Dec. 25, 2012

(54) ***BACILLUS THURINGIENSIS* STRAIN FOR INHIBITING INSECT PESTS**

(75) Inventors: Ching-Chou Tzeng, Taichung County (TW); Suey-Sheng Kao, Taichung County (TW)

(73) Assignee: Taiwan Agricultural Chemicals and Toxic Substances Research Inst., Council of Agriculture, Taichung County (TW)

( * ) Notice: Subject to any disclaimer, the term of this patent is extended or adjusted under 35 U.S.C. 154(b) by 892 days.

This patent is subject to a terminal disclaimer.

(21) Appl. No.: 12/345,055

(22) Filed: Dec. 29, 2008

(65) Prior Publication Data

US 2009/0165359 A1    Jul. 2, 2009

(30) Foreign Application Priority Data

Dec. 31, 2007  (TW) .............................. 96151628 A (51) Int. Cl.
*C12N 1/00* (2006.01)

(52) U.S. Cl. .......................... 435/243; 435/4; 435/252.5

(58) Field of Classification Search .................. 435/243, 435/4, 252.5

See application file for complete search history.

(56) References Cited

U.S. PATENT DOCUMENTS

| 5,827,514 | A | 10/1998 | Bradfisch et al. | |
|---|---|---|---|---|
| 5,965,428 | A | 10/1999 | Gilmer et al. | |
| 6,500,617 | B1 * | 12/2002 | Stemmer et al. | .................. 506/1 |
| 7,070,982 | B2 | 7/2006 | Malvar et al. | |

FOREIGN PATENT DOCUMENTS

TW            224139       5/1994

OTHER PUBLICATIONS

Martinez et al. "Contents of cry genes and insecticidal toxicity of *Bacillus thuringiensis* strains from terrestrial and aquatic habitats", J of Applied Microbiology, 2002, 92:745-752.*
Classification of Insects: 1 page, 2011.*
Martinez et al., Association analysis between serotype, cry gene content, and toxicity to *Helicoverpa armigera* larvae among *Bacillus thuringiensis* isolates native to Spain, J. Invertebr Pathol. (2005) 90(2):91-97.
Microbial Pest Control Agent *Bacillu thuringiensis*, World Health Organization Geneva (1999).
Hofte, H., H.R. Whiteley. Insecticidal crystal proteins of *Bacillus thuringiensis*. Microbiol. Rev., 1989, vol. 53: pp. 242-255.

Gill, S.S., E.A. Cowles, P.V. Pietrantonio. The mode of action of *Bacillus thuringiensis* endotoxins. Annu. Rev. Entomol. 1992, vol. 37: pp. 615-636.
Gleave, A.P., R. Williams, R.J. Hedges. Screening by polymerase chain reaction of *Bacillus thuringiensis* serotypes for the presence of cry V-like insecticidal protein genes and characterization of a cry V gene cloned from *B. thuringiensis* subsp. kurstaki. Appl. Environ. Microbiol. 1993, vol. 59: pp. 1683-1687.
Lereclus, D., A. Delecluse, M-M. Lecadet. Diversity of *Bacillus thuringiensis* toxins and genes. pp. 37-69 in "*Bacillus thuringiensis*, An Environmental Biopesticide: Theory and Practice", P.F. Entwistle, J.S. Cory, J.J. Bailey, S. Higgs Eds. John Wiley and Sons Ltd. Press, England 1993.
Shin, B.S., S.H. Park, S.K. Choi, B.T. Koo, S.T. Lee, J.I. Kim. Distribution of cryV-type insecticidal protein genes in *Bacillus thuringiensis* and cloning of cryV-type genes from *Bacillus thuringiensis* subsp. kurstaki and *Bacillus thuringiensis* subsp. entomocidus. Appl. Environ. Microbiol, 1995, vol. 61: pp. 2402-2407.
Kostichka, K., G.W. Warren, M. Mullins, A.D. Mullins, J.A. Craig, M.G. Koziel, J.J. Estruch. Cloning of a cryV-type insecticidal protein gene from *Bacillus thuringiensis*: the cryV-encoded protein is expressed early in stationary phase. J. Bacteriol, 1996, vol. 178: pp. 2141-2144.
Akiba, Y., K. Katoh. Microbial ecology of *Bacillus thuringiensis* V. Selective medium for *Bacillus thuringiensis* vegetative cells. Appl. Entomol Zool, 1986, vol. 21: pp. 210-215.
Travers, R.S., P.a. W. Martin, C.F. Reichelderfer. Selective process for efficient isolation of soil *Bacillus* spp. Appl. Eviron. Microbiol., 1987, vol. 53: pp. 1263-1266.
Chak, K.F., Y.M. Yang. Characterization of the *Bacillus thuringiensis* strains isolated from Taiwan. Proc. Natl. Sci. Counc.B. ROC, 1990, vol. 14: pp. 175-182.
Chilcott, C.N., P.J. Wigley. Isolation and toxicity of *Bacillus thuringiensis* from soil and insect habitats in New Zealand. J. Invertebr. Pathol. 1993, vol. 61: pp. 244-247.
Kao, S.S., C.C. Tzeng, S.J. Tuan, Y.S. Tsai. Isolation, characterization and cry gene typing of *Bacillus thuringiensis* isolates from stored product material samples collected around Taiwan, 1996, pp. 132-151. Proceedings, The Second Pacific Rim Conference on Biotechnology of *Bacillus thuringiensis* and its Impact to the Environment. Nov. 4-8, 1996. Chaing Mai, Thailand.
Kalman S., K.L. Kiehne, J.L. Libs, T. Yamamoto. Cloning of a novel crylC-type gene from a strain of *Bacillus thuringiensis* subsp. galleriae. Appl. Environ. Microbiol., 1993, vol. 59: pp. 1131-1137.
Chen, W.R., G.C. Li, S.S. Kao, Y.M. Tzeng, C.C. Tzeng. Cloning and expression of the insecticidal crystal protein gene, CryIA5, of *Bacillus thuringiensis* D4-01 from Taiwan. Plant Prot. Bull, 2006, vol. 48: pp. 17-30 (in Chinese) (English abstract of this paper is on p. 30 thereof).

* cited by examiner

*Primary Examiner* — Susan Hanley
*Assistant Examiner* — Bin Shen
(74) *Attorney, Agent, or Firm* — Volpe and Koenig, P.C.

(57) ABSTRACT

A novel bacterial strain of *Bacillus thuringiensis* for inhibiting insect pests is provided, wherein the *Bacillus thuringiensis* includes the fragments of cry1Aa, a cry1Ab, a cry1C, a cry1D and a cry1F genes.

17 Claims, 4 Drawing Sheets

*B. thuringiensis*
A603

M 800
700 — cry1Aa (724 bp)
600
500
400 — cry1D (414 bp)
— cry1F (368 bp)
300 — cry1C (288 bp)
— cry1Ab (238 bp)
200

BACILLUS THURINGIENSIS STRAIN FOR INHIBITING INSECT PESTS

FIELD OF THE INVENTION

The present invention relates to a novel microorganism of *Bacillus thuringiensis*. In particular, the present invention relates to a microorganism of *Bacillus thuringiensis* having fragments of cry1Aa, cry1Ab, cry1C, cry1D and cry1F genes.

BACKGROUND OF THE INVENTION

Along with the respect to life quality and the rise of environmental protection consciousness, at present, the trend that the biological insecticides are substituted for the traditional pesticides to prevent the ultimate accumulation in the food chain has become the mainstream, in which *Bacillus thuringiensis* is the most famous application in the biological insecticides, and is easily utilized and safe.

*Bacillus thuringiensis*, a Gram-positive rod bacterium, is an insectile pathogenic bacterium. *B. thuringiensis* will progress into the non-mitotic semi-stationary phase or differentiate to form the spore or the insecticidal crystal protein while lacking nutrient or staying in the worse environment. The insecticidal crystal protein produced from *B. thuringiensis* can inhibit the growth of some insect pests, but is not harmful to mammals and birds. Therefore, scientists have been isolated various insecticidal genes from *B. thuringiensis*, and developed as the recombinant genetic products.

The endotoxin gene of *B. thuringiensis* is located on the plasmid thereof, so as to proceed the generic engineering easily. In the early stage, the recombinant endotoxin genes almost are limited in the cloning of single gene fragment. Recently, the multiple endotoxin genes or the genes with large diversities, even the chimeric genes, are utilized so as to improve the insecticidal effect, enlarge the insecticidal area or modify the resistance of *B. thuringiensis* to the worse environment.

The parental relationships among various endotoxin proteins of *B. thuringiensis* are different because of the insecticidal crystal proteins produced from the divergent nucleotide sequences of plasmids thereof. The insecticidal targets also are different, which are classified as six groups (Hofte and Whiteley, 1989; Gill et al., 1992; Gleave et al., 1993; Lereclus et al., 1993; Shin et al., 1995; and Kostichka et al., 1996). Among these literatures, Cry1 protein family has the insecticidal effect to Lepidoptera; Cry2 protein family shows the insecticidal effect to Lepidoptera and Diptera, or only has the insecticidal effect to Diptera; Cry3 protein family has the insecticidal effect to Coleoptera; and Cry4 protein family only has the insecticidal effect to Diptera. Cry5 protein family cannot form as crystal protein, whereas Lepidoptera and Coleoptera can be killed by some part of Cry5 proteins but cannot be killed by other part thereof. CytA protein does not have specific insecticidal scope; however, the cytolytic and hemolytic effects can be induced by CytA protein. The cry1 gene of *B. thuringiensis* encodes the longest amino acid sequence, but cytA gene thereof encodes the shortest one.

U.S. Pat. Nos. 5,827,514 and 5,965,428 respectively disclose Cry1Ac and Cry1F chimeric proteins with different fragments for insecticidal function. U.S. Pat. No. 7,070,982 further discloses the composite proteins of Cry1Ab, Cry1Ac and Cry1F. Taiwan Patent No. 224139 further discloses a single bacterial strain containing cry1Aa, cry1Ab, cry1C and cry1D gene fragments. From the abovementioned references, the insecticidal effect of the multiple endotoxin gene products is large better than the function of the single endotoxin gene product for antagonizing insect pests.

Therefore, scientists are still exploring the microorganism with multiple endotoxin genes isolated by generic engineering or isolated by natural selection.

It is therefore attempted by the applicant to deal with the above situation encountered in the prior art.

SUMMARY OF THE INVENTION

In accordance with the first aspect of the present invention, an isolated microorganism of *Bacillus thuringiensis* for inhibiting an insect is provided. The microorganism includes fragments of a cry1Aa, a cry1Ab, a cry1C, a cry1D and a cry1F genes.

Preferably, the isolated microorganism further includes a fragment of a cry1Ad1 gene.

Preferably, the insect has an order of Lepidoptera and a family being one selected from a group consisting of Noctuidae, Pyralidae, Tortricidae and Plutellidae.

Preferably, the family of Noctuidae includes a species being one selected from a group consisting of *Spodoptera exigua*, *Spodoptera litura* and *Trichoplusia ni*; the family of Pyralidae includes a species being one of *Maruca vitrata*, *Ephestia cautella* Walker; the family of Tortricidae includes a species of *Adoxophyes orana*; and the family of Plutellidae includes a species of *Plutella xylostella*.

In accordance with the second aspect of the present invention, a pesticidal composition including *Bacillus thuringiensis* is provided. *B. thuringiensis* has fragments of a cry1Aa, a cry1Ab, a cry1C, a cry1D and a cry1F genes.

Preferably, the pesticidal composition further includes an effective dosage of an endotoxin, and the endotoxin further is a δ-endotoxin.

Preferably, the pesticidal composition further includes a pharmaceutically acceptable carrier.

Preferably, the endotoxin has at least a translated product of a cry1Ad1 gene, and the endotoxin is produced by *Bacillus thuringiensis*.

Preferably, *B. thuringiensis* further includes a fragment of a cry1Ad1 gene.

In accordance with the third aspect of the present invention, an inhibition method for an insect is provided. The inhibition method includes a step of applying *Bacillus thuringiensis* comprising fragments of a cry1Aa, a cry1Ab, a cry1C, a cry1D and a cry1F genes on a specific target.

Preferably, *B. thuringiensis* has an effective dosage for inhibiting the insect.

Preferably, the specific target is one selected from a group consisting of a crop, a cultivated land and a combination thereof.

In accordance with the fourth aspect of the present invention, an isolated microorganism of *Bacillus thuringiensis* having a DSM Accession No. 21764 is provided.

Preferably, the isolated microorganism further has a function being one selected from a group consisting of inhibiting an insect, producing a metabolite for antagonizing the insect, and being a raw material of a composition for inhibiting the insect.

Preferably, the metabolite is an endotoxin.

The bacterial strain of *Bacillus thuringiensis* A603 was deposited in the Deutsche Sammlung von Mikroorganismen und Zellkulturen (DSMZ) GmbH, Inhoffenstr. 7B, D-38124 Braunschweig, Germany, on Aug. 21, 2008, under the rules of Budapest Treaty, and the deposit number was DSM 21764.

The above objectives and advantages of the present invention will become more readily apparent to those ordinarily

DETAILED DESCRIPTION OF THE PREFERRED EMBODIMENT

Figure 1:
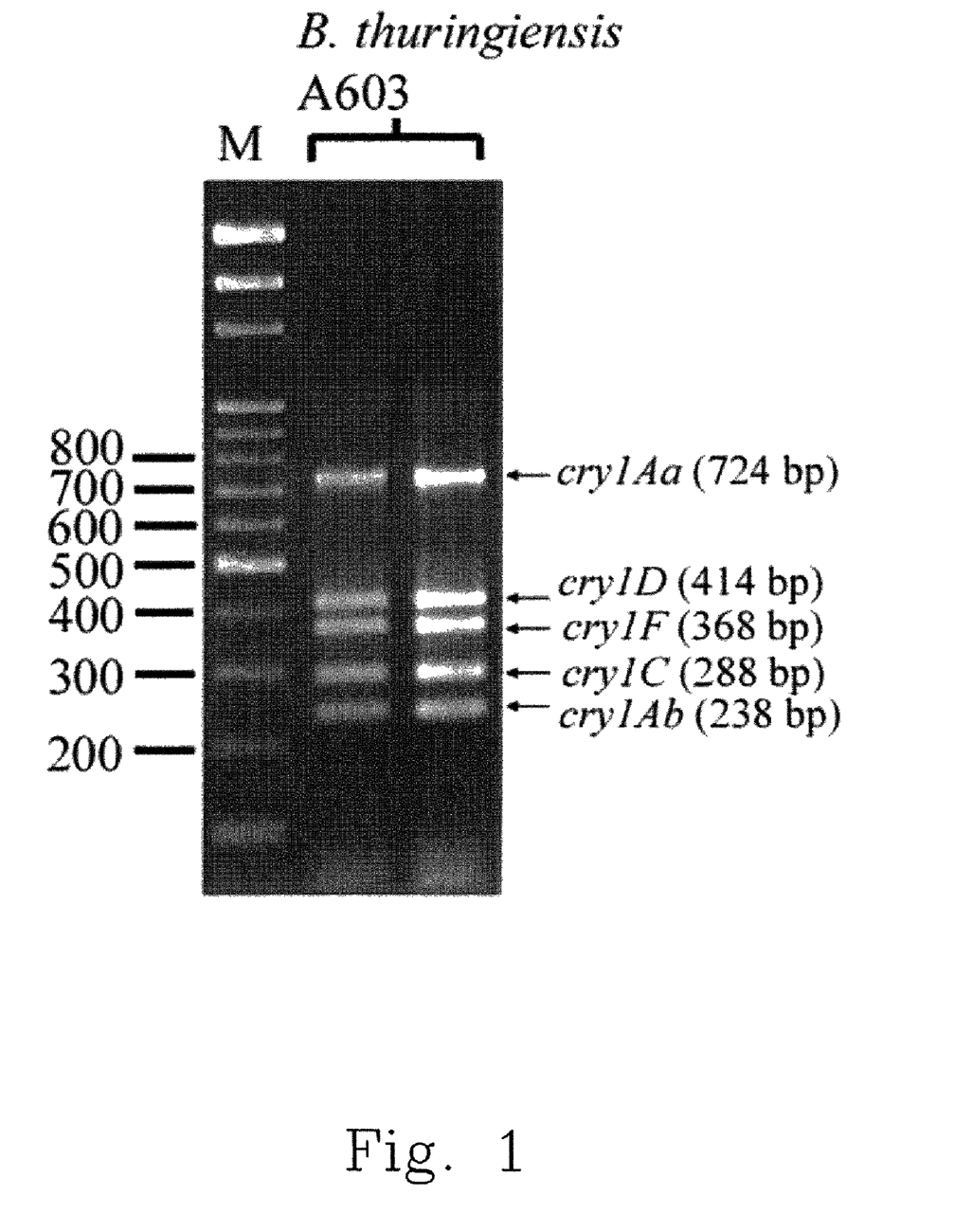
FIG. 1 is the electrophoresis pattern showing the endotoxin gene types of *B. thuringiensis* A603 strain of the present invention, and the endotoxin genes thereof are amplified by PCR.
Figure 2:
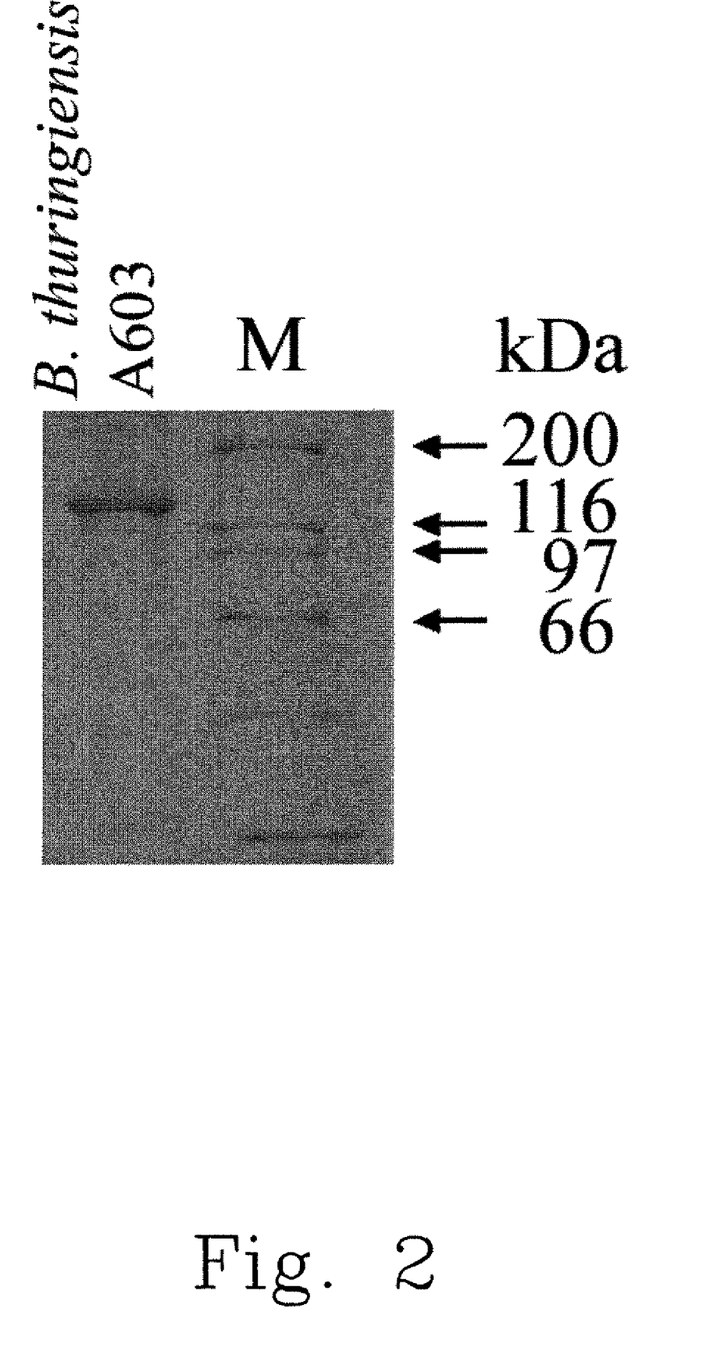
FIG. 2 is the electrophoresis pattern showing the endotoxin proteins of *B. thuringiensis* A603 strain.
Figure 3:
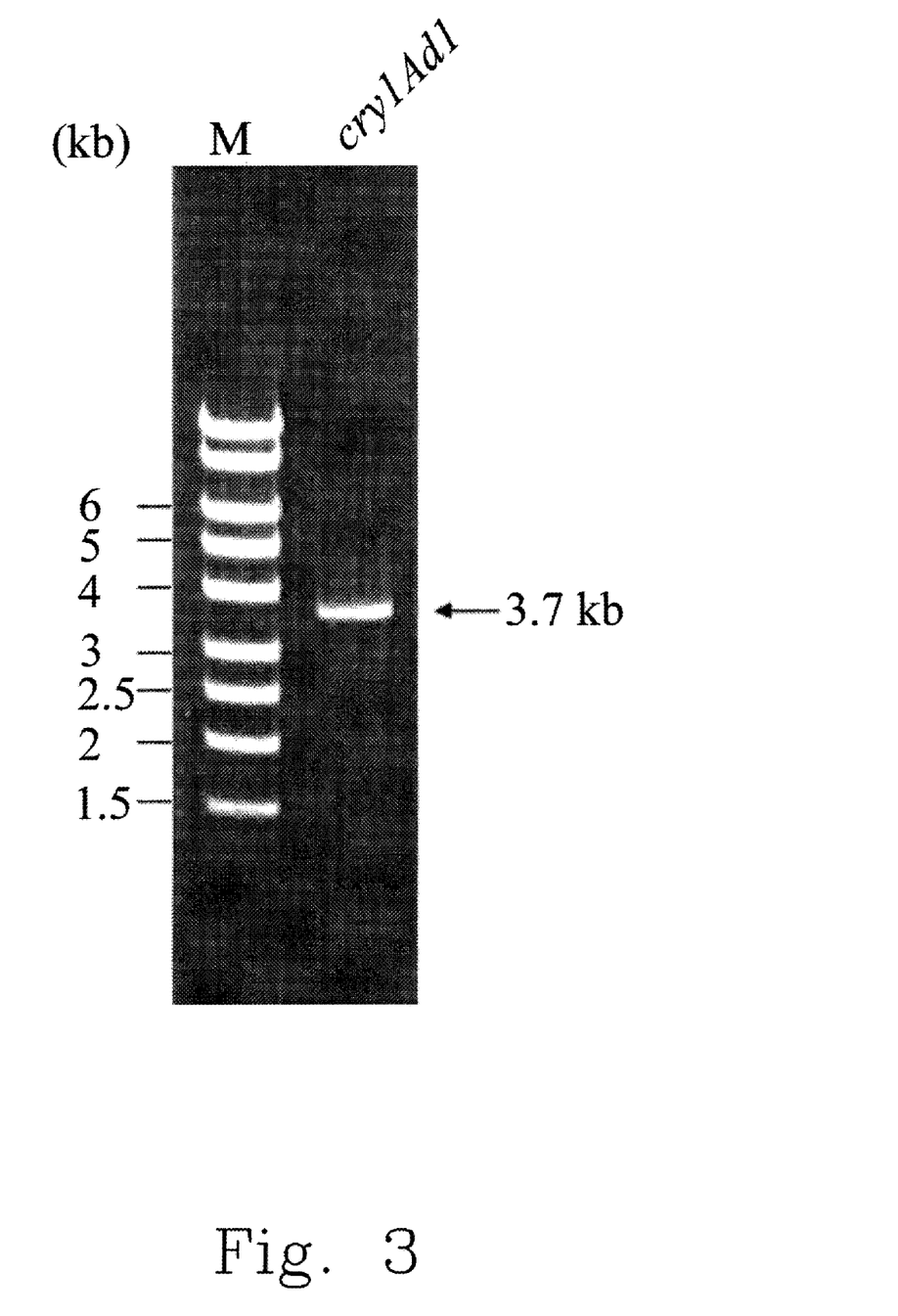
FIG. 3 is the electrophoresis pattern showing cry1Ad1 gene amplified by PCR.
Figure 4:
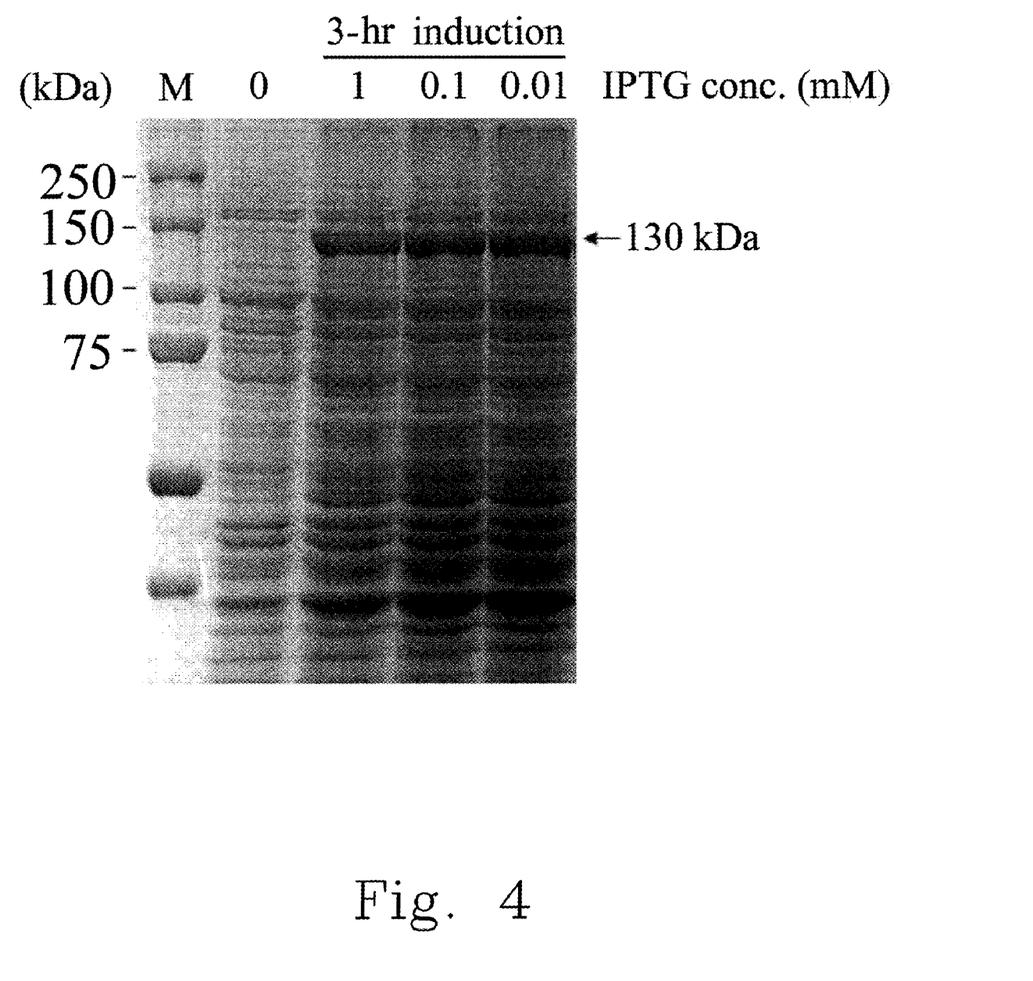
FIG. 4 is the expression pattern of Cry1Ad1 protein induced with different concentrations of IPTG.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

A novel microorganism of *Bacillus thuringiensis* is provided in the present invention, and the bacterial strain can inhibit the growth of insect pests. The following detail descriptions illustrate the source, purification and isolation, identification and inhibition effect to the targeted pests of *B. thuringiensis*.

Sampling of Microorganism

Dust sample is collected in the granary of Baojhong Township Farmers' Association in Yunlin County, Taiwan. Ten gram of each sample is collected and then is packaged in the plastic bag for reserving at 4° C.

Isolation and Identification of Microorganism

Each sample of 0.5 g is suspended and vortexed in 10 ml of distilled water, and each sample is isolated in accordance with the methods published in the literatures of Akiba and Katch (1986), Travers et al. (1987), Chak and Yang (1990), and Chilcott and Wigley (1993). The heat-treated suspended samples are sprayed on the nutrient agar (NA) plates. After the continuous incubation at 28° C. for five days, the isolation of single colony is performed. The nutrient agar plates are observed under the phase contrast microscope with the oil immersion lens with a magnification of 1,500×, for isolating the bacterial strain containing crystal protein and spore. The isolated bacterial strains are nominated respectively and reserved at 4° C. (Kao et al., 1996).

Incubation of Microorganism

Each of the nominated bacterial strains is suspended in distilled water, and is incubated on the nutrient agar plates by streaking method for three times, to isolate and identify the bacterial strain un-polluted. Each single colony is inoculated in 5 ml of Luria-Bertani (LB) broth (containing 1% of Bacto-tryptone, 0.5% of Bacto-yeast extract and 1% of NaCl, pH 7.0), and incubated overnight at 28° C. at 250 rpm. The incubated broth of 0.5 ml is sub-cultured at a ratio of 1:10 in the same condition for 3 hours.

Identification of Bacterial Strain

The sub-cultured bacterial strains are analyzed, and one of the bacterial strains is selected to nominated as *B. thuringiensis* A603, which is analyzed for the bacterial morphology and the follow-up experiments.

Polymerase Chain Reaction (PCR) of DNA and Cloning of Plasmid

The endotoxin gene types of *B. thuringiensis* A603 strain of the present invention are identified in accordance with the combinations of the endotoxin-specific primers published in Kalman et al. (1993).

(1) Amplification of cry1Aa Gene Fragment

The annealing reaction and amplification of PCR are performed by the cry1 specific sequence as the reverse primer (i.e. SEQ ID NO. 1) and the cry1Aa specific sequence as the forward primer (i.e. SEQ ID NO. 2), to identify the existence of the cry1Aa gene fragment.

(2) Amplification of cry1Ac Gene Fragment

The annealing reaction and amplification of PCR are performed by the cry1 specific sequence as the reverse primer (i.e. SEQ ID NO. 1) and the cry1Ac specific sequence as the forward primer (i.e. SEQ ID NO. 3), to identify the existence of the cry1Ac gene fragment.

(3) Amplification of cry1B Gene Fragment

The annealing reaction and amplification of PCR are performed by the cry1 specific sequence as the reverse primer (i.e. SEQ ID NO. 1) and the cry1B specific sequence as the forward primer (i.e. SEQ ID NO. 4), to identify the existence of the cry1B gene fragment.

(4) Amplification of cry1C Gene Fragment

The annealing reaction and amplification of PCR are performed by the cry1 specific sequence as the reverse primer (i.e. SEQ ID NO. 1) and the cry1C specific sequence as the forward primer (i.e. SEQ ID NO. 5), to identify the existence of the cry1C gene fragment.

(5) Amplification of cry1D Gene Fragment

The annealing reaction and amplification of PCR are performed by the cry1 specific sequence as the reverse primer (i.e. SEQ ID NO. 1) and the cry1D specific sequence as the forward primer (i.e. SEQ ID NO. 6), to identify the existence of the cry1D gene fragment.

(6) Amplification of cry1E Gene Fragment

The annealing reaction and amplification of PCR are performed by the cry1 specific sequence as the reverse primer (i.e. SEQ ID NO. 1) and the cry1E specific sequence as the forward primer (i.e. SEQ ID NO. 7), to identify the existence of the cry1E gene fragment.

(7) Amplification of cry1F Gene Fragment

The annealing reaction and amplification of PCR are performed by the cry1 specific sequence as the reverse primer (i.e. SEQ ID NO. 1) and the cry1F specific sequence as the forward primer (i.e. SEQ ID NO. 8), to identify the existence of the cry1F gene fragment.

(8) Amplification of cry1Ab Gene Fragment

The annealing reaction and amplification of PCR are performed by the cry1Ab forward specific sequence as the forward primer (i.e. SEQ ID NO. 9) and the cry1Ab reverse specific sequence as the reverse primer (i.e. SEQ ID NO. 10), to identify the existence of the cry1Ab gene fragment.

(9) Full-Length Amplification of cry1Ad1 Gene and Cloning of Plasmid

The inventors further desire to obtain the cry1Ab gene fragment for the gene recombination experiment. The forward primer (1A29A) (SEQ ID NO. 11): 5'-ttaacacccct ggatccaaaattgatattt-3' (underlined is BamHI restriction enzyme site), and the reverse primer (1Ab37B1) (SEQ ID NO. 12): 5'-tttgcatgcatatattattcctccataagaagtaatt-3' (underlined is SphI restriction enzyme site) (Chen et al., 2006) are designed to perform the annealing reaction and amplification of PCR. An unexpected band different from the cry1Ab gene fragment shown on the electrophoresis pattern is founded.

Therefore, the plasmid of *B. thuringiensis* A603 strain is being the template, and the full-length of the unexpected band is amplified by using SEQ ID NO. 11 and SEQ ID NO. 12 as primers. The gene fragment of band is constructed into an intermediate pSC-A vector by StrataClone PCR Cloning Kit (Stratagen), then the full-length sequencing is performed by the large fragment nucleoside sequencing (i.e. primer walking). The sequencing result is analyzed and compared by computer, and the band is identified as cry1Ad1 gene and the full length is 3704 base pairs (bp). Accordingly, the expression plasmid is nominated as pSC-A-cry1Ad1.

(10) Expression of Cry1Ad1 Protein cry1Ad1 gene is digested from pSC-A-cry1Ad1 plasmid by BamHI and SphI endonucleases, then is constructed into the expression vector pQE82. Further, the expression plasmid pQE82-cryAd1 is transformed into *Escherichia coli* BL21 for further protein expression.

Combinations of Endotoxin Genes in *B. thuringiensis* A603 Strain

Please refer to FIG. 1, which is the electrophoresis pattern showing the endotoxin gene types of *B. thuringiensis* A603 strain of the present invention, and the endotoxin genes thereof are amplified by PCR. According to Kalman et al. (1993), the lengths of the anticipated specific fragments of cry1Aa, cry1Ac, cry1B, cry1C, cry1D, cry1E, cry1F and cry1Ab genes respectively are 724, 487, 830, 288, 414, 883, 368 and 238 bp. Therefore, *B. thuringiensis* A603 strain of the present invention includes multiple endotoxin fragments of cry1Aa, cry1Ab, cry1C, cry1D and cry1F genes in accordance with the fragment lengths shown in FIG. 1. In addition, the DNA ladder in FIG. 1 is abbreviated as "M", and the unit of base pair is abbreviated as bp.

Please refer to FIG. 2, which is the electrophoresis pattern showing the endotoxin proteins of *B. thuringiensis* A603 strain. *B. thuringiensis* A603 strain actually can express endotoxin protein, which has the molecular weight of 130 kilodaltons (kDa), in accordance with the result shown in FIG. 2. Furthermore, the endotoxin protein expressed in *B. thuringiensis* A603 strain actually has inhibition activity on insect pests from the in vitro experiment of endotoxin activity (data not shown). In addition, the protein marker in FIG. 2 is abbreviated as "M", and the unit is kilodalton (kDa).

Please refer to FIG. 3, which is the electrophoresis pattern showing cry1Ad1 gene amplified by PCR. The full length of cry1Ad1 gene is 3704 bp, and the sequencing result is referring to SEQ ID NO. 13 in the sequence list. The DNA ladder in FIG. 3 is abbreviated as "M", and the unit is kilo base pair (kb). The Cry1Ad1 expression pattern induced with different concentrations of isopropyl β-D-1-thiogalactopyranoside (IPTG) after the transformation of the expression plasmid into *E. coli* BL21 is shown in FIG. 4. Cry1Ad1 protein actually can be abundantly expressed. Further, endotoxin expressed by *B. thuringiensis* A603 strain actually has inhibition activity on insect pests from the in vitro experiment of endotoxin activity (data not shown). The protein marker in FIG. 4 is abbreviated as "M", and the unit is kilodalton (kDa).

Inhibition Activity of *B. thuringiensis* A603 to Targeted Insect Pests

A composition with the insecticidal ability is further provided in the present invention, wherein the composition includes a culture of the effective dosage of *B. thuringiensis* A603 and the acceptable carrier. Further, endotoxin is included in the culture. *B. thuringiensis* A603 or its mutant of the present invention is enriched by adapting industrial standard incubation method and fermentation. The fermented culture is tested to confirm the inhibition effect to the targeted insect pests.

Embodiment 1

*Spodoptera exigua*

After *B. thuringiensis* A603 is enriched, five liters of the fermented culture is serially-diluted. *Spodoptera exigua* larvae in the early third instars nymph are treated with different diluted concentrations of fermented culture continuously for 120 hours by using feed mixture method. Twenty larvae are tested in each group, feed is renovated, and the observation is continued. The numbers of dead larvae before and after the treatment of *B. thuringiensis* A603 are recorded, and the mortality of *S. exigua* larvae is calculated.

Please refer to Table 1, which is the inhibition activity of *B. thuringiensis* A603 fermented culture to *S. exigua*. *B. thuringiensis* A603 actually has the lethal effect to *S. exigua* in accordance with the result in Table 1.

TABLE 1

Inhibition activity of *B. thuringiensis* A603 fermented culture to *Spodoptera exigua*

| Dilution Rate | No. of tested insects | Mortality (%) |
|---|---|---|
| Control (water) | 20 | 0 |
| 350 (~140 IU/mg*) | 20 | 90 |
| 700 (~700 IU/mg) | 20 | 95 |
| 1400 (~35 IU/mg) | 20 | 80 |
| 2800 (~17.5 IU/mg) | 20 | 70 |
| 5600 (~8.75 IU/mg) | 20 | 20 |

*Sample valence (IU/mg) = [(50% of lethal concentration ($LC_{50}$) of Bta standard)/($LC_{50}$ of sample)] × (sample valence of Bta standard (IU/mg)). The tested insect is *Trichoplussia ni*.

Embodiment 2

*Spodoptera litura*

The preparation of the diluted fermented *B. thuringiensis* A603 cultures is identical with Embodiment 1. *S. litura* larvae in the early third instars nymph are treated with different diluted concentrations of fermented culture continuously for 120 hours by using feed mixture method. Twenty larvae are tested in each group, feed is renovated, and the observation is continued. The growth results, such as weight of larvae and number of dead larvae, before and after the treatment of *B. thuringiensis* A603 are recorded.

Please refer to Table 2, which is the inhibition activities of (A) the B. thuringiensis A603 fermented culture and (B) the commercialized product, DIPEL® (a microorganism of *Bacillus thuringiensis* var. kurstaki HD-1), respectively to *S. litura*. The average weight of *S. litura* larva before the treatment is 0.0025 g. The average weight of larva before the treatment divided by that of larva after the treatment equals to the growth ratio. The average weight of control group minus that of treatment group equals to a difference of average weight, which divided by the average weight of control group equals to the inhibition rate (%). According to the result in Table 2, the growth ratio of larvae treated with *B. thuringiensis* A603 is less than that of larvae treated with DIPEL® under the identical dilution rate. In the meantime, the inhibition rate of *B. thuringiensis* A603 to *S. litura* is also higher than that of DIPEL® to *S. litura*. Accordingly, *B. thuringiensis* A603 actually has the inhibition ability to *S. litura* larvae.

TABLE 2

Inhibition activities of (A) the *B. thuringiensis* A603 fermented culture and (B) the commercialized product, DIPEL ®, respectively to *S. litura*.

| Dilution rate | No. of tested larvae | Mortality (%) | Larva weight (g/No. of larvae) | Growth ratio | Inhibition rate (%) |
|---|---|---|---|---|---|
| (A) *B. thuringiensis* A603 ||||||
| Control (water) | 30 | 0 | 0.033 | 13.3 | 0 |
| 350 (140 IU/mg*) | 20 | 75 | 0.002 | 0.96 | 93 |
| 700 (~70 IU/mg) | 20 | 50 | 0.005 | 1.8 | 86 |
| (B) Commercialized product, DIPEL ® ||||||
| Control (water) | 30 | 0 | 0.033 | 13.3 | 0 |
| 350 (140 IU/mg) | 20 | 65 | 0.004 | 1.48 | 89 |
| 700 (~70 IU/mg) | 20 | 50 | 0.005 | 1.83 | 86 |

*Sample valence (IU/mg) = [(50% of lethal concentration ($LC_{50}$) of Bta standard)/($LC_{50}$ of sample)] × (sample valence of Bta standard (IU/mg)). The tested insect is *Trichoplussia ni*.

Embodiment 3

*Maruca vitrata*

The preparation of the diluted fermented *B. thuringiensis* A603 cultures is identical with Embodiment 1. *M. vitrata* larvae in the early second and early third instars nymphs respectively are treated with different diluted concentrations of fermented culture continuously for 120 hours by using feed mixture method. Five larvae are tested in each concentration, feed is not renovated, and the observation is continued. The number of dead larvae are recorded from 24th to 120th hours.

From the distribution result of mortality in Table 3, almost 50% inhibition ability of *B. thuringiensis* A603 to *M. vitrata* larvae is achieved after the larvae are treated with *B. thuringiensis* A603 for 96 hours and in the low treatment concentration.

TABLE 3

Mortality of *B. thuringiensis* A603 fermented culture to *M. vitrata*

| Concen- tration (ppm) | (%) Mortality ||||||||||
|---|---|---|---|---|---|---|---|---|---|---|
|  | 24 Hr || 48 Hr || 72 Hr || 96 Hr || 120 Hr ||
|  | 2nd* | 3rd | 2nd | 3rd | 2nd | 3rd | 2nd | 3rd | 2nd | 3rd |
| 60 | 0 | 0 | 20 | 20 | 60 | 60 | 100 | 100 | 100 | 100 |
| 30 | 0 | 0 | 0 | 20 | 40 | 40 | 100 | 80 | 100 | 80 |
| 15 | 0 | 0 | 0 | 0 | 40 | 20 | 60 | 40 | 100 | 80 |
| 7.5 | 0 | 0 | 0 | 0 | 20 | 20 | 60 | 40 | 80 | 40 |
| 3.75 | 0 | 0 | 0 | 0 | 20 | 20 | 40 | 40 | 80 | 40 |
| Control (water) | 0 | 0 | 0 | 0 | 0 | 0 | 0 | 0 | 0 | 0 |

*instar nymph

Embodiment 4

*Ephestia cautella* Walker

The preparation of the diluted fermented *B. thuringiensis* A603 cultures is identical with Embodiment 1. *E. cutella* Walker larvae after hatching for 14 days are treated with different diluted concentrations of fermented culture continuously for 120 hours by using feed mixture method. Ten larvae are tested in each concentration, and each concentration is tested for triplet. Feed is not renovated, and the observation is continued. Further, the common commercialized product, Dipel®, is tested simultaneously. The number of dead larvae after 120 hours is recorded.

*B. thuringiensis* A603 has a better inhibition ability to *E. cautella* Walker than the commercialized product, Dipel®, from the result of mortality in Table 4.

TABLE 4

Mortality of *B. thuringiensis* A603 fermented product inhibiting *E. cautella* Walker.

| Dilution Rate | Mortality (%) |||
|---|---|---|---|
|  | *B. thuringiensis* A603 | Dipel ® | Control (CK) |
| 10 | 63 | 60 | 0 |
| 100 | 57 | 40 | 0 |

Embodiment 5

*Adoxophyes orana*

The preparation of the diluted fermented *B. thuringiensis* A603 cultures is identical with Embodiment 1. *A. orana* larvae in the early third instars nymph are treated with different diluted concentrations of fermented culture continuously for 120 hours by using feed mixture method. Ten larvae are tested in each concentration, and each concentration is tested for triplet. Feed is not renovated, and the observation is continued. The number of dead larvae are recorded, and the mortality of larvae is calculated.

From the result of mortality in Table 5, 50% inhibition ability of *B. thuringiensis* A603 to *A. orana* larvae is achieved after the larvae are treated with *B. thuringiensis* A603 for 144 hours and in the low treatment concentration.

TABLE 5

Mortality of *B. thuringiensis* A603 fermentative product to *A. orana*

| Concen- tration of treatment (ppm) | Mortality (%) after different treatment time |||||
|---|---|---|---|---|---|
|  | 120 Hr | 144 Hr | 168 Hr | 192 Hr | 216 Hr |
| 60 | 73 | 77 | 77 | 83 | 87 |
| 30 | 67 | 67 | 67 | 70 | 77 |
| 15 | 50 | 57 | 63 | 63 | 73 |
| 7.5 | 60 | 67 | 67 | 67 | 73 |
| 3.75 | 47 | 47 | 57 | 60 | 67 |
| 1.875 | 43 | 50 | 53 | 53 | 60 |
| Control (water) | 0 | 0 | 0 | 0 | 0 |

Embodiment 6

*Plutella xylostella*

The preparation of the diluted fermented *B. thuringiensis* A603 cultures is identical with Embodiment 1. *P. xylostella* larvae in the early third instars nymph are treated with different diluted concentrations of fermented culture continuously for 72 hours by using feed mixture method. Ten larvae are tested in each concentration, and each concentration is tested for five repetitions. Feed is renovated, and the observation is continued. The number of dead larvae after 72-hour treatment are recorded, and the mortality of larvae is calculated.

From the result of mortality in Table 5, *B. thuringiensis* A603 actually has inhibition ability to *P. xylostella*.

TABLE 6

Mortality of *B. thuringiensis* A603 fermented product to *P. xylostella*.

| Concentration (ppm) | Mortality (%) of *P. xylostella* |
|---|---|
| 40 | 98 |
| 20 | 84 |
| 10 | 48 |
| Control (water) | 0 |

Embodiment 7

*Trichoplusia ni*

The preparation of the diluted fermented *B. thuringiensis* A603 cultures is identical with Embodiment 1. *T. ni* larvae in the early second instars nymph are treated with different diluted concentrations of fermented culture continuously for 72 hours by using feed mixture method. Ten larvae are tested in each concentration, and each concentration is tested for five repetitions. Feed is renovated, and the observation is continued. The number of dead larvae after 72-hour treatment are recorded, and the lethality of larvae is calculated.

From the result of lethality in Table 7, *B. thuringiensis* A603 has better inhibition ability to *T. ni* larvae than the commercialized products, XENTARI® (a biological insecticide of *Bacillus thuringiensis*, subsp. *aizawai*, Strain ABTS-1857; Valent Bioscience Corp., IL, U.S.A.) and DIPEL®.

TABLE 7

Lethality of *B. thuringiensis* A603 fermented product to *T. ni* larvae

| Concentration (ppm) | Lethality (%) | | |
|---|---|---|---|
| | *B. thuringiensis* A603 | XENTARI® | DIPEL® |
| 30 | 50 | 28 | 42 |
| 15 | 34 | 20 | 30 |
| Control (water) | 0 | 0 | 0 |

In conclusion, the isolated *Bacillus thuringiensis* A603 of the present invention indeed is a novel bacterial strain of *Bacillus thuringiensis*, which contains endotoxin fragments of cry1Aa, cry1Ab, cry1C, cry1D, cry1F and cry1Ad1 genes. Further, the bacterial strain of *B. thuringiensis* has inhibition ability to the insect pests, such as *Spodoptera exigua*, *Spodoptera litura*, *Trichoplusia ni*, *Maruca vitrata*, *Ephestia cautella* Walker, *Adoxophyes orana* and *Plutella xylostella*, etc.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. An isolated microorganism of *Bacillus thuringiensis* for inhibiting an insect, wherein the microorganism comprises a cry1Aa, a cry1Ab, a cry1C, a cry1D, a cry1Ad1 and a cry1F genes.

2. The isolated microorganism according to claim 1, wherein the insect has an order of Lepidoptera and a family being one selected from a group consisting of Noctuidae, Pyralidae, Tortricidae and Plutellidae.

3. The isolated microorganism according to claim 2, wherein the insect having the family of Noctuidae comprises a species being one selected from a group consisting of *Spodoptera exigua, Spodoptera litura* and *Trichoplusia ni*.

4. The isolated microorganism according to claim 2, wherein the insect having the family of Pyralidae comprises a species being one of *Maruca vitrata, Ephestia cautella* Walker.

5. The isolated microorganism according to claim 2, wherein the insect having the family of *Tortricidae* comprises a species of *Adoxophyes orana*.

6. The isolated microorganism according to claim 2, wherein the insect having the family of *Plutellidae* comprises a species of *Plutella xylostella*.

7. A pesticidal composition comprising *Bacillus thuringiensis* having a cry1Aa, a cry1Ab, a cry1C, a cry1D, a cry1Ad1 and a cry1F genes.

8. The pesticidal composition according to claim 7 further comprising an effective dosage of an endotoxin.

9. The pesticidal composition according to claim 8 further comprising a pharmaceutically acceptable carrier.

10. The pesticidal composition according to claim 8, wherein the endotoxin is a δ-endotoxin.

11. The pesticidal composition according to claim 8, wherein the endotoxin has at least a translated product of the cry1Ad1 gene.

12. The pesticidal composition according to claim 8, wherein the endotoxin is produced by *Bacillus thuringiensis*.

13. An inhibition method for an insect, comprising a step of:
applying *Bacillus thuringiensis* comprising a cry1Aa, a cry1Ab, a cry1C, a cry1D, a cry1Ad1 and a cry1F genes on a specific target, wherein the *Bacillus thuringiensis* has an effective dosage for inhibiting the insect.

14. The inhibition method according to claim 13, wherein the specific target is one selected from a group consisting of a crop, a cultivated land and a combination thereof.

15. An isolated microorganism of *Bacillus thuringiensis* having a DSM Accession No. 21764.

16. The isolated microorganism according to claim 15 further having a function being one selected from a group consisting of inhibiting an insect, producing a metabolite for antagonizing the insect, and being a raw material of a composition for inhibiting the insect.

17. The isolated microorganism according to claim 16, wherein the metabolite is an endotoxin.

* * * * *

SEQUENCE LISTING

```
<160> NUMBER OF SEQ ID NOS: 13

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
atcactgagt cgcttcgcat gtttgacttt ctc                                  33

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
gagccaagca gctggagcag tttacacc                                        28

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
```

-continued tcacttccca tcgacatcta cc                                        22

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gtcaacctta tgagtcacct gggcttc                                   27

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
caacctctat ttggtgcagg ttc                                       23

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
ggtacattta gatattcaca gccac                                     25

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
cttagggata aatgtagtac ag                                        22

<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
ccggtgaccc attaacattc caatc                                     25

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
ggtcgtggct atatccttcg tgtcacagc                                 29

<210> SEQ ID NO 10
<211> LENGTH: 23
<212> TYPE: DNA
<213> ORGANISM: Artificial Sequence

```
<220> FEATURE:
<223> OTHER INFORMATION: Primer

<400> SEQUENCE: 10
gaattgcttt cataggctcc gtc                                              23

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ttaacaccct ggatccaaaa ttgatatttt                                       29

<210> SEQ ID NO 12
<211> LENGTH: 37
<212> TYPE: DNA
<213> ORGANISM: Artificial Sequence
<220> FEATURE:
<223> OTHER INFORMATION: Primer

<400> SEQUENCE: 12
tttgcatgca tatattattc ctccataaga agtaatt                               37

<210> SEQ ID NO 13
<211> LENGTH: 3704
<212> TYPE: DNA
<213> ORGANISM: Bacillus thuringiensis

<400> SEQUENCE: 13
ttaacaccct ggatccaaaa ttgatattta gtaaattcgg ttg

```
cttggttcag gcccaaataa tcagaacctg tttgtccttg atggaacgga attttctttt    1320
gcctccctaa cagccgattt accttctact atatacagac aaaggggaac ggtcgattca    1380
ctagatgtaa taccgccaca ggataatagt gtgccagcac gtgcgggatt tagtcatcga    1440
ttaagtcatg ttacaatgct gagccaagca gctggagcag tttacacctt gagagctcca    1500
acgttttctt ggcgacatcg tagtgctgaa ttctctaacc taattccttc atcacaaatc    1560
acacagatac ctttaacaaa gtctattaat cttggctctg ggacctctgt tgttaaagga    1620
ccaggattta caggaggaga tattcttcga agaacttcac ctggccagat ttcaacctta    1680
agagtgacta ttactgcacc attatcacaa agatatcgcg taagaattcg ctacgcttct    1740
actacaaatt tacaattcca tacatcaatt gacggaagac ctattaatca ggggaatttt    1800
tcagcaacta tgagtagtgg gggtaattta cagtccggaa gctttaggac tgcaggtttt    1860
actactccgt ttaactttc aaatggatca agtatattta cgttaagtgc tcatgtcttc    1920
aattcaggca atgaagttta tatagatcga attgaatttg ttccggcaga agtaacattt    1980
gaggcggaat atgatttaga aagagcgcaa gaggcggtga atgctctgtt tacttcttcc    2040
aatcaactag gattaaaaac aaatgtgacg gactatcata ttgatcaagt gtccaatcta    2100
gtcgaatgtt tatccggtga attctgtctg gatgaaaaga gagaattgtc cgagaaagtc    2160
aaacatgcga agcgactcag tgatgagcgg aatttacttc aagacccaaa cttcagaggc    2220
atcaatagac aaccagaccg tggctggaga ggcagtacgg atattaccat ccaaggagga    2280
gatgacgtat tcaaagagaa ttacgtcaca ctaccgggta cctttaatga gtgttatcct    2340
acgtatctgt atcaaaaaat agtgagtcg aaattaaaag cctatacccg ttaccaatta    2400
agagggtaca tcgaggatag tcaagactta gaaatctatt taattcgcta caatacaaaa    2460
cacgaaacag taaatgtgcc aggtacgggt tccttatggc cgctttcagt cgaaaatcca    2520
attggaaagt gcggagaacc aaatcgatgc gcaccacaac ttgaatggaa tcctgatcta    2580
gattgttcct gcagagacgg ggaaaaatgt gcacatcact cccatcattt ctccttggac    2640
attgatattg gatgtacaga tttaaatgag aacttaggtg tatgggtgat attcaaaatt    2700
aagacgcaag atggtcacgc aagactaggt aatctagagt ttctcgaaga gaaaccatta    2760
gtaggcgaat cgttagcacg cgtgaagaga gcggagaaga agtggagaga caaacgagag    2820
aaattgcaag tggaaacaaa tatcgtttat aaagaggcaa aagaatctgt agatgcttta    2880
tttgtgaact ctcaatatga tagattacaa gcggataccg acatcgcgat gattcatgcg    2940
gcagataaac gcgttcatcg aattcgagaa gcatatcttc cagagttatc tgtaattccg    3000
ggtgtcaatg cgggcatttt tgaagaatta gagggacgta ttttcacagc ctactcttta    3060
tatgatgcga gaaatgtcat taaaaatggc gatttcaata atggcttatc atgctggaac    3120 gtgaagggc atgtagatgt agaagaacaa acaaccacc gttcggttct tgttgtcccg    3180
gaatgggaag cagaggtgtc acaagaggtt cgtgtctgtc caggtcgtgg ctatatccta    3240
cgtgttacag cgtacaaaga gggatatgga gaaggttgcg taacgattca tgagatcgaa    3300
gacaatacag acgaactgaa attcagcaac tgtgtagaag aggaagtata tccaaacaac    3360
acggtaacgt gtaatgatta tactgcaaat caagaagaat acggggtgc gtacacttct    3420 cgtaatcgtg gatatggtga atcttatgaa agtaattctt ccataccagc tgagtatgcg    3480
ccagtttatg aggaagcata tatagatgga agaaaagaga atccttgtga atctaacaga    3540
```

-continued

```
ggatatgggg attacacgcc actaccagct ggttatgtga caaaagaatt agagtacttc    3600
ccagaaaccg ataaggtatg gattgagatc ggggaaacgg aaggaacatt catcgtggat    3660
agcgtggaat tacttcttat ggaggaataa tatatgcatg caaa                     3704
```